United States Patent [19]
Tobe et al.

[11] Patent Number: 5,721,206
[45] Date of Patent: Feb. 24, 1998

[54] PHARMACEUTICAL COMPOSITION FOR USE AS A RETINAL PIGMENT EPITHELIAL CELL GROWTH AGENT

[75] Inventors: Takao Tobe, Osaka; Kanji Takahashi, Hirakata; Hiroshi Ohkuma, Nara; Masanobu Uyama, Kyoto, all of Japan

[73] Assignee: Toray Industries, Inc., Tokyo, Japan

[21] Appl. No.: 404,597

[22] Filed: Mar. 15, 1995

[51] Int. Cl.⁶ .................................................. A61K 37/00
[52] U.S. Cl. ............................. 514/2; 514/885; 514/912
[58] Field of Search ............................ 514/2, 885, 913

[56] References Cited

PUBLICATIONS

Medline Abstract of Ophthalmic Research (1994) 26 (1) 1–7.
Medline Abstract of ACTA Neurologica Belgica (1994). Lyon–Caen et al.
WPID 147503, 1988.

Tobe et al., Journal of Japanese Opthalmological Society, vol. 98, Supplement, Abstract T1–51 (Mar. 15, 1995).
Tobe et al., J. Japanese Ophthalmological Society 99(5):558–570 (1995).
Tobe et al., J. Japanese Ophthalmological Society 99(7):792–805 (1995).
Tobe et al., J. Japanese Ophthalmological Society 99(5):571–581 (1995).
Tobe et al., "Influence on Reconstruction Process of Choriocapillaris After Photocoagulation of Retina by Interferon–$\beta$" (Sep. 17, 1993).

*Primary Examiner*—Zohreh Fay
*Attorney, Agent, or Firm*—Birch, Stewart, Kolasch & Birch, LLP

[57] ABSTRACT

A pharmaceutical composition for use as a retinal pigment epithelial cell growth stimulating agent comprising an interferon and a pharmaceutically acceptable carrier is disclosed. The composition is useful as a therapeutic agent for oculopathies, such as pigmentary retinal degeneration, central chorioretinopathy, and macular dystrophy.

10 Claims, No Drawings

PHARMACEUTICAL COMPOSITION FOR USE AS A RETINAL PIGMENT EPITHELIAL CELL GROWTH AGENT

FIELD OF THE INVENTION

This invention relates to a novel therapeutic agent for oculopathies which is clinically and experimentally useful as a medicine and a reagent.

BACKGROUND OF THE INVENTION

Vision is the most important of senses, and visual disability such as loss of vision and blindness is considered as a serious physical disability. In particular, an increase of visual function disturbance accompanying aging is a concern in the coming aging society. The importance of improving the quality of life of patients suffering from diseases that impair their daily lives has recently been stressed in the treatment of such diseases. From this standpoint, for patients suffering from oculopathies, improvement and maintenance of visual function are essential requirements for improvement in their quality of life. It is of urgent necessity to establish a medical treatment which satisfies these requirements.

Serious visual loss or blindness may ensue from various causes. The causes which are liable to directly lead to such visual disability are retinochoroidal diseases, that is, diseases leading to degeneration of retinal pigment epithelial cells, such as retinal hemorrhage, retinal edema, retinal detachment, retinochoroiditis, and retinal atrophy. The treatment of choice in the management of these diseases includes drug therapy, laser photocoagulation, and vitreous surgery, but none of these has yet achieved results on a satisfactory level. Therefore, development of a more effective treatment has keenly been demanded. In particular, considering that laser photocoagulation or vitreous surgery is accompanied by invasion, drug therapy has great advantages such as little invasion and easy management. However, presently there are few medications of high utility.

On the other hand, with the advent of experimental and clinical studies, conditions of retinochoroidal diseases have been recently elucidated to reveal not only lesions of the visual cells of the retina but nerve fiber disorders, circulation disorders in the retina, and lesions of the choroid and retinal pigment epithelium.

It has turned out that retinal pigment epithelial (hereinafter abbreviated as RPE) cells play an important role in the maintenance of visual cells. RPE cells are aligned in a layer on the Bruch's membrane to form the pigment epithelium, the outermost layer of the retina. The pigment epithelium not only serves to absorb the light having reached the retina, thereby to prevent reflection, but performs complicated and important biochemical functions, participating in nourishment and reproduction of visual cells. It also functions as a partition between visual cells and the choriocapillaries together with the Bruch's membrane and builds up a blood-retinal barrier.

Further, RPE cells can produce both a growth factor and an inhibitor of neovascularization. RPE cells control onset, development, suppression and retraction of choroidal neovascularizations, as reviewed by Uyama Masanobu in *Journal of Japanese Ophthalmological Society*, 95, 1145–1180 (1991, hereby incorporated in its entirety by reference).

Physiological and pathological studies of cultures of RPE cells having the above-mentioned functions would be of great use for the study of physiological functions and pathology of eyes. Study of factors that modify the functions of RPE cells has only recently started, yielding preliminary results that interleukin (IL-)-1β, IL-6, IL-8, tumor necrosis factor (TNF), granulocytemacrophage colony stimulating factor (GM-CSF), monocyte chemotactic protein (MCP), basic fibroblast growth factor (bFGF), etc. stimulate growth of RPE cells and that transforming growth factors (TGFs) inhibit growth of RPE cells (see Tamai Shin, *Journal of Japanese Ophthalmological Society*, 97, 1–2 (1993), hereby incorporated in entirety by reference).

All of these modifying factors were discovered because of their physiological activities observed in other evaluation systems but with no attention being paid to the functions of RPE cells per se. Therefore, it is not likely that these factors exert their action selectively on RPE cells.

As mentioned above, a satisfactory treatment of retinochoroidal diseases has not yet been established despite concern about retinochoroidal diseases causing serious reduction in visual functions or blindness, the occurrences of which may increase in the future. Histological and functional studies on RPE cells which seem to influence the pathology of the diseases have also begun, as have studies of treatment or prevention of retinochoroidal diseases utilizing growth or activation of RPE cells.

Among the diseases involving degeneration of RPE cells (i.e., retinochoroidal diseases), pigmentary retinal degeneration is a hereditary disease. Symptomatic treatment using a vasodilator or vitamin D is the only treatment method available, and there is no great improvement. Retinal pigment epitheliopathy also has no effective drug therapy. It is believed that a factor which stimulates the growth and activation of RPE cells would be useful as a medication effective on these diseases.

Laser photocoagulation sometimes has a therapeutic effect on retinochoroidal degeneration accompanied by neovascularization, whereas the currently available drug therapy does not offer a radical cure for this disease. While laser photocoagulation has an effect of coagulating blood vessels, since the action of thermal coagulation reaches to the inner layers of the retina, with consequent impairment of the function of the retina, it cannot be applied to cases involving the macular fovea, which is a portion of the retina very important in central visual acuity. Where choroidal neovascularization occurs in the vicinity of the fovea centralis, the result of photocoagulation treatment is unsatisfactory. Further, recurrence of neovascularization after photocoagulation is significant. In order to overcome these disadvantages of photocoagulation, effective drug therapy has been demanded. Since it is known that RPE cells produce neovascularization inhibitory factors while they are growing (according to the review by Uyama), RPE cell growth factors are expected to be applicable as neovascularization inhibitors.

Because RPE cells play a major role in maintaining the tissue and function of the retina and the choroid as mentioned above, degeneration and hypofunction of RPE cells are considered to lead to serious retinochoroidal diseases. Accordingly, it seems that retinochoroidal diseases should be treated by stimulating growth and activation of RPE cells, but no medicine has been developed with this purpose.

SUMMARY OF THE INVENTION

The problem to be solved is to develop a compound or composition for stimulating RPE cell growth and activation as a therapeutic agent of retinochoroidal diseases which have resisted conventional drug therapy.

Development of drug therapy that increases the treatment effect of laser photocoagulation is also a significant problem. In coagulating neovascularizations, adjunct neovascularization inhibitory activity is expected from the compound or composition for stimulating RPE cell growth that solves the problem. Where photocoagulation is performed on primary and secondary retinal detachment, a medicine which would enhance the treatment effect is a solution. Thus, it is a problem waiting for solution to develop a novel compound or composition for stimulating RPE cell growth which can conveniently be applied to intractable diseases such as degeneration of the retinal pigment epithelium (especially in the vicinity of the macular fovea), retinochoroidal atrophy, and retinal detachment.

Accordingly, an object of the present invention is to solve the above problems and to provide an industrially and medically useful compound or composition for stimulating RPE cell growth. It is another object of the invention to provide a medically useful compound or composition for inhibiting retinal neovascularization.

The above objects of the present invention are accomplished by a RPE cell growth-stimulating composition containing interferon as an active ingredient.

DETAILED DESCRIPTION OF THE INVENTION

The oculopathies to which the present invention applies broadly include retinochoroidal atrophy, such as pigmentary retinal degeneration, Oguchi's disease, angioid streaks of the retina, retinal pigment epitheliopathy, acute multifocal posterior retinal pigment epitheliopathy, multifocal posterior retinal pigment epitheliopathy, central serous chorioretinopathy, central exudative chorioretinopathy, macular hole, myopic macular atrophy, and macular dystrophy (Stargardt's disease, egg-yolk macular degeneration).

Interferons (hereinafter abbreviated as IFN) which can be used in the present invention may be any of $\alpha$- type, $\beta$-type and $\gamma$-type, may be either of consensus type or hybrid type and may be of natural type, recombinant type or chemically synthetic type. Natural type IFN-$\beta$ is preferred. Hematopoietic cells and established cell lines thereof are preferably used as IFN-$\alpha$ or IFN-$\beta$-producing cells, and fibroblasts and established cell lines thereof are preferably used as IFN-$\beta$-producing cells.

In preparing IFN by recombinant DNA techniques, usable host cells include cells of mammals, e.g., CHO (Chinese hamster ovary) cells and mouse C127 cells; insects, e.g., silkworms and cabbage armyworms (*Manestra brassicae*); and microorganisms, e.g., *Escherichia coli, Bacillus subtilis,* and yeast. Mice, rats, hamsters, rabbits, goats, sheep, swine, and cattle are also useful. The production of recombinant IFN is considered known in the art.

Crude IFN thus prepared is isolated from the preparation system, such as conditioned medium of a cell culture, an insect extract, a microbial cell extract or a tissue extract, by various column chromatographic techniques. Any column having affinity for IFN may be used. Suitable columns include those packed with silicon dioxide (silica) beads or calcium phosphate (hydroxylapatite) beads, those using heparin, a dye or a hydrophobic group as a ligand, metal chelate columns, ion-exchange columns, and gel filtration columns. Purifications of interferons are considered known in the art.

In the present invention, IFN can be administered orally or parenterally either as such or as a pharmaceutical composition together with pharmaceutically acceptable carriers, excipients, etc.

Dose forms for oral administration include tablets, pills, capsules, granules, syrups, emulsions and suspensions. These dose forms are prepared in a conventional manner and contain carriers or excipients commonly employed in the art. For example, carriers or excipients for tablets include lactose, maltose, sucrose, starch, and magnesium stearate.

Dose forms for parenteral administration include eye drops, ointments, injections, poultices, liniments, suppositories, nasals, inhalants, and transdermals. Liquid preparations are prepared in a conventional manner by, for example, dissolving or suspending IFN in a sterile aqueous solution for injection or in an extract and, if desired, emulsifying to incorporate IFN into liposomes. Solid preparations are prepared in a conventional manner by, for example, mixing with excipients such as mannitol, trehalose, sorbitol, lactose, and glucose, followed by freeze-drying. The freeze-dried preparation may be powdered for use. Gel preparations are prepared in a conventional manner by, for example, dissolving IFN in a thickening agent, e.g., glycerin, polyethylene glycol, methyl cellulose, carboxymethyl cellulose, hyaluronic acid or chondroitin sulfate, or a polysaccharide.

All the above preparations may contain a stabilizer, such as human serum albumin, human immunoglobulin, $\alpha$2-macroglobulin, and amino acids. They may further contain a dispersant or an absorption accelerator selected from alcohols, sugar alcohols, ionic surface active agents, non-ionic surface active agents and so forth as far as the physiological activities of IFN are not impaired. If desired, trace metals and organic acid salts may be added to the preparations.

In the present invention, natural type IFN-$\beta$ is preferentially used. Natural type IFN-$\beta$ can usually be obtained as follows. IFN-$\beta$-producing cells having been cultured on the surface of glass, plastics or a DEAE-dextran microcarrier are subjected to induction by synthetic double stranded RNA, such as poly(inosinic acid-cytidylic acid) (poly I:C), and then to superinduction (for example, metabolic inhibition using a combination of cycloheximide and actinomycin D or ultraviolet irradiation). The thus treated cells are cultured in a medium for 20 to 48 hours to produce and accumulate IFN-$\beta$.

Since the resulting culture generally has a low IFN-$\beta$ concentration and contains many contaminants of cell or additive origin, the IFN-$\beta$ should be concentrated and purified for medical use. While the method for concentrating IFN-$\beta$ is not particularly limited, chromatography using a blue dye-bound insoluble carrier and a metal chelate-bound carrier are preferred. That is, a crude IFN-$\beta$-containing liquid is brought into contact with a blue dye-bound insoluble carrier, and IFN-$\beta$ is recovered as a solution in an eluent. The resulting IFN-$\beta$ solution is then brought into contact with a metal (e.g., zinc) chelate-bound carrier to recover concentrated and purified IFN-$\beta$ as an eluate. Details of the conditions for blue dye and metal chelate chromatography of IFN are known in the art. The purified IFN-$\beta$ preparation is formulated into the above-described dose form for use as a therapeutic agent for oculopathies.

A suitable dose is appropriately decided depending on the disease, the age, body weight and conditions of a patient, the dose form, and the administration route, and usually ranges from 1 to 10,000,000 international units (IU)/day, preferably from 100 to 6,000,000 IU/day. Dosages can be set per kilogram of body weight ranging from 0.02 to 500,000 IU/kg per day, preferably 2 to 300,000 IU/kg per day, still more preferably 2 to 30,000 IU/kg per day. It is expected that routes of administration that provide the composition directly to the eye will require dosages tending to the low end of the ranges noted.

The present invention will now be illustrated in greater detail with reference to Examples, but it should be understood that the present invention is not to be construed as being limited thereto.

EXAMPLE I

Photocoagulation using an intense krypton layer beam was performed on the fundi of 19 eyes of 10 rhesus monkeys to experimentally damage the RPE and induce choroidal neovascularization. Twelve eyes of 6 animals out of 10 were grouped as an IFN-treated group, and the rest (7 eyes of 4 animals) as a control group. Each animal of the IFN-treated group was intramuscularly injected with natural IFN-$\beta$ (produced by Toray Industries, Inc.) at a dose of 50 to 120,000 IU/kg for 14 consecutive days, beginning one week after the photocoagulation. The control group was subjected to photocoagulation without further treatment.

Each group was subjected to ophthalmoscopic examination and fluorescein angiography 2 and 3 weeks after the photocoagulation to observe the state of choroidal neovascularizations. After 3 weeks from the photocoagulation, the eye balls were enucleated, and the retinal pigment epithelium was morphologically observed under an optical microscope and a transmission electron microscope.

The control group showed 40 occurrences of choroidal neovascularization. The observation after 3 weeks from photocoagulation revealed that 8 out of 40 (20%) spontaneously retracted, 16 out of 40 (40%) were unchanged, and the rest (40%) showed development. On the other hand, the IFN-treated group showed 55 occurrences of choroidal neovascularization, 13 of which (24%) spontaneously retracted, 34 of which (62%) were unchanged, and the rest (14%) developed. The difference between the two groups is statistically significant, proving that IFN administration inhibits development of choroidal neovascularization. Histologic examination by optical and electron microscopic observation of the lesions in the IFN group showed retraction of neovascularizations and also growth of RPE cells around the neovascularizations.

It is seen that IFN exhibits inhibitory activity on neovascularization per se and in addition has an activity of activating and stimulating proliferation of RPE cells to thereby produce therapeutic effects on damage of the retinal pigment epithelium and neovascularization.

The composition stimulating RPE cell growth, containing IFN as an active ingredient, is useful as a therapeutic agent for oculopathies, such as pigmentary retinal degeneration, central chorioretinopathy, and macular dystrophy.

EXAMPLE II

Experimental choroidal neovascularization in rhesus monkey eyes was produced by strong photocoagulation with a krypton laser. The choroidal neovascularization was confirmed by normal and fluorescein angiographies one week after the photocoagulation. Rhesus monkeys received intramuscular administration of IFN-$\beta$ at $3 \times 10^6$ IU/day for group A and at $6 \times 10^6$ IU/day for group B for 14 days.

The efficacy of IFN-$\beta$ was evaluated with the angiographies three weeks after the photocoagulation. Then eye balls were removed and examined histologically by optical and electron microscopy.

The growth of neovascular vessels in the IFN-treated group is suppressed compared with that in the control group. Histologically, neovascular membranes seemed to be surrounded early and tightly by RPE cells in IFN-treated group more than in the control group.

Thus, IFN-$\beta$ may act not only endothelial cells but also RPE cells to suppress the extension of choroidal neovascular vessels.

While the invention has been described in detail and with reference to specific examples thereof, it will be apparent to one skilled in the art that various changes and modifications can be made therein without departing from the spirit and scope of the invention.

What is claimed is:

1. A method for treating degeneration of retinal epithelial cells or neovascularization of retinal epithelia comprising administering to a subject suffering from degeneration of retinal epithelial cells or neovascularization of retinal epithelia a composition comprising an amount of interferon effective to stimulate growth and activation of retinal pigment epithelial cells and a pharmaceutically acceptable carrier.

2. The method of claim 1, wherein said composition is administered by intramuscular injection.

3. The method of claim 1, wherein said interferon is an interferon-$\beta$.

4. The method of claim 1, wherein said interferon is isolated from a medium used to culture fibroblast cells.

5. The method of claim 1, wherein said interferon is administered in a dose of from 1 to 10,000,000 International Units.

6. The method of claim 1, wherein said interferon is administered in a dose of from 100 to 6,000,000 International Units.

7. The method of claim 3, wherein said interferon is administered in a dose of from 1 to 10,000,000 International Units.

8. The method of claim 3, wherein said interferon is administered in a dose of from 100 to 6,000,000 International Units.

9. The method of claim 4, wherein said interferon is administered in a dose of from 1 to 10,000,000 International Units.

10. The method of claim 4, wherein said interferon is administered in a dose of from 100 to 6,000,000 International Units.

* * * * *